United States Patent
Wang

(10) Patent No.: US 8,571,678 B2
(45) Date of Patent: Oct. 29, 2013

(54) ADAPTATION OF MODULATION PARAMETERS FOR COMMUNICATIONS BETWEEN AN IMPLANTABLE MEDICAL DEVICE AND AN EXTERNAL INSTRUMENT

(75) Inventor: Yu Wang, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1294 days.

(21) Appl. No.: 12/365,052

(22) Filed: Feb. 3, 2009

(65) Prior Publication Data

US 2010/0198304 A1    Aug. 5, 2010

(51) Int. Cl.
*A61N 1/08* (2006.01)

(52) U.S. Cl.
USPC ............ 607/60; 607/31; 607/32; 607/59

(58) Field of Classification Search
USPC .................. 607/60, 32, 59, 27, 31
See application file for complete search history.

(56) References Cited

U.S. PATENT DOCUMENTS

| | | | |
|---|---|---|---|
| 5,630,836 A * | 5/1997 | Prem et al. | 607/61 |
| 6,443,891 B1 | 9/2002 | Grevious | |
| 7,023,359 B2 | 4/2006 | Goetz et al. | |
| 7,139,283 B2 | 11/2006 | Quigley et al. | |
| 7,177,698 B2 | 2/2007 | Klosterman et al. | |
| 7,392,092 B2 | 6/2008 | Li et al. | |
| 7,397,859 B2 | 7/2008 | McFarland | |
| 8,108,048 B2 * | 1/2012 | Masoud | 607/60 |
| 2005/0010269 A1 * | 1/2005 | Lebel et al. | 607/60 |
| 2006/0161223 A1 * | 7/2006 | Vallapureddy et al. | 607/60 |
| 2007/0123946 A1 * | 5/2007 | Masoud | 607/32 |
| 2007/0279149 A1 | 12/2007 | Dal Molin | |
| 2008/0037411 A1 | 2/2008 | Niemela et al. | |
| 2010/0161004 A1 * | 6/2010 | Najafi et al. | 607/60 |

FOREIGN PATENT DOCUMENTS

| | | |
|---|---|---|
| EP | 1151759 | 11/2001 |
| WO | 0224064 | 3/2002 |
| WO | WO2008060197 | * 5/2008 |

OTHER PUBLICATIONS

PCT/US2010/022735 International Search Report and Written Opinion mailed Sep. 28, 2010.

* cited by examiner

*Primary Examiner* — Kennedy Schaetzle
(74) *Attorney, Agent, or Firm* — Withers & Keys, LLC

(57) ABSTRACT

External instruments and implantable medical devices communicate using modulation parameter settings that may be adapted during communication sessions based on a quality of the wireless communications link. An analysis of the quality of the link is performed and a request to change modulation parameters is sent to one of the devices by the other. The analysis may be based on measuring noise and interference during idle communication frames. The devices may then change the modulation parameter settings, for the uplink, downlink, or both. The devices may also employ a recovery operation to revert back to the previous modulation parameter settings if the transmissions are not properly received using the changed modulation parameter settings. The modulation parameter settings may include modulation type, modulation symbol rate, and the like.

24 Claims, 13 Drawing Sheets

APPLICATION

| | | LINK QUALITY | MODULATION TYPE | MODULATION SYMBOL RATE | |
|---|---|---|---|---|---|
| | 1 | A-B | X | K | ← 708 |
| | 2 | A-B | X | L | ← 710 |
| | 1 | B-C | Y | K | |
| | 2 | B-C | Z | K | |
| | 1 | C-D | Y | L | |
| | 2 | C-D | Z | K | |
| | 1 | D-E | Z | M | |
| | 2 | D-E | Z | M | |

702 — LINK QUALITY
704 — MODULATION TYPE
706 — MODULATION SYMBOL RATE
700

FIG. 7

ADAPTATION OF MODULATION PARAMETERS FOR COMMUNICATIONS BETWEEN AN IMPLANTABLE MEDICAL DEVICE AND AN EXTERNAL INSTRUMENT

TECHNICAL FIELD

Embodiments are related to communications occurring between an implantable medical device and an external instrument. More particularly, embodiments are related to that adaptation of modulation parameters for such communications.

BACKGROUND

Implantable medical devices (IMD) provide medical functions to patients. Examples of these functions include defibrillator shocks, muscle and neurological tissue stimulation, and physiological sensing. The IMD device may communicate with an external instrument (EI) such as a device programmer from time to time for various reasons. For instance, the IMD may transfer to the EI data that has been collected over a given period of time. As another example, the EI may transfer stimulation parameter settings to the IMD.

The communications between the EI and the IMD utilize modulation of a carrier signal to convey information. The modulation has various parameters. One parameter is the modulation type which pertains to how the information is represented on the carrier signal. Another parameter is the modulation symbol rate which pertains to how quickly the information is being conveyed by the carrier signal. Conventionally, modulation parameters such as these are fixed because once the modulation parameters are chosen and put into use, they are not subsequently changed.

Communicating with fixed modulation parameters between the IMD and the EI has various drawbacks. For instance, if the communication signals could support a higher symbol rate than what has been chosen at any given point during a communication session, then the communication session will take longer than if a higher symbol rate had been chosen. Likewise, if the communication signals are not adequately exchanged due to a chosen symbol rate being too high at any given point during a communication session, then the session may fail altogether and/or numerous re-attempts may result in the session taking longer than if a lower symbol rate had been chosen.

Similar issues exist for modulation type as well, where a given modulation type may support a higher throughput at a given point in time during a communication session but a less efficient modulation type has instead been chosen which may lead to a longer communication session. As another example, a given modulation type may support a more reliable exchange of information at a given point in time during a communication session but a less reliable modulation type has instead been chosen which may result in a failed communication session and/or a longer communication session.

IMDs have a limited amount of electrical power available in an on-board battery. Sending and receiving information consumes a significant amount of that electrical power. Therefore, exchanges of information between an EI and an IMD are one factor that constrains the length of time that the IMD can operate before exhausting the on-board battery.

SUMMARY

Embodiments address issues such as these and others by providing adaptation of modulation parameters during communications between implantable medical devices and external instruments. The quality of the communication link may be analyzed while communications are on-going and modulation parameter settings may be changed to adapt to the quality at a given time.

Embodiments include a method of adapting communications between an implantable medical device and an external instrument. The method involves transferring communication signals using a first initial modulation parameter setting over a telemetry link between the implantable medical device and the external instrument. The method involves analyzing a quality metric of the communication signals that have been transferred and selecting a second modulation parameter setting as a replacement for the first initial modulation parameter setting in response to the analysis. The method further involves transferring communication signals using the second modulation parameter setting over the telemetry link between the implantable medical device and the external instrument.

Embodiments include an external instrument for communicating with an implantable medical device. The external instrument includes communication circuitry with selectable modulation parameter settings for exchanging communication signals with the implantable medical device. The external instrument also includes analysis logic circuitry that is coupled to the communication circuitry and that performs a link quality analysis of communication signals that are received using a first initial modulation parameter setting and that selects a second modulation parameter setting to replace the first initial modulation parameter setting in subsequent exchanges of communication signals with the implantable medical device.

Embodiments include an implantable medical device for communicating with an external instrument. The implantable medical device includes communication circuitry with selectable modulation parameter settings for exchanging communication signals with the external instrument. The implantable medical device includes medical application circuitry that performs medical tasks. Additionally, the implantable medical device includes control circuitry that is coupled to the communication circuitry to obtain operational instructions from received communication signals. The control circuitry instructs the communication circuitry to utilize modulation parameter settings that are specified by the operational instructions that pertain to modulation. The control circuitry is also coupled to the medical application circuitry and instructs the medical application circuitry to utilize medical task parameter settings that are specified by the operational instructions.

DESCRIPTION OF THE DRAWINGS

FIG. 7 shows one example of a look-up table that may be utilized by a device acting as a master for the communications when selecting a modulation parameter setting based on a current telemetry link quality.

DETAILED DESCRIPTION

Embodiments provide adaption of modulation parameter settings during communication sessions between an external instrument (EI) and an implantable medical device (IMD). The modulation parameter settings may include changing the settings for any number of modulation parameters. The modulation parameter settings may be changed for various reasons, such as to find a modulation parameter setting that improves throughput, improves reliability, and so forth.

Figure 1:
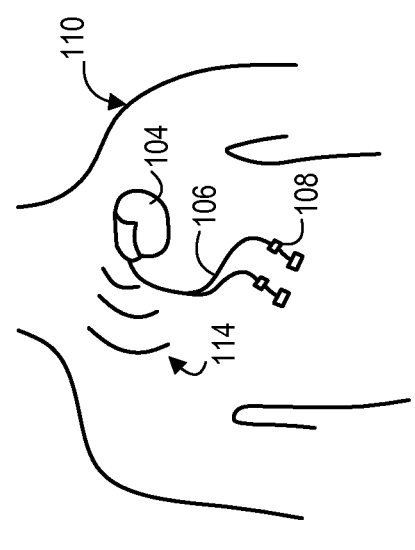
FIG. 1 shows an operating environment for embodiments of external instruments and implantable medical devices.
Figure 1:
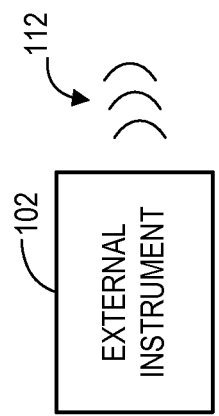

FIG. 1 shows one example of an operating environment for the various embodiments. As shown, the EI 102 communicates by sending wireless telemetry signals 112 to an IMD 104 present at a body 110 of a patient. The EI 102 to IMD 104 path is known as the downlink. The IMD 104 communicates by sending wireless telemetry signals 114 to the EI 102, and the IMD 104 to EI 102 path is known as the uplink. The communication signals being exchanged may carry data used for many purposes. The data may represent programming or parameter settings sent by the EI 102 that are received and implemented by the IMD 104. The data may represent physiological measurements made by the IMD 104 that are sent to the EI 102 for analysis and review by clinicians.

The EI 102 may be of various forms. For example, the EI 102 may be an external device programmer that allows a clinician to select medical tasks to be performed by the IMD 104, to select medical task parameter settings that control the performance of medical tasks, and so forth. EI 102 could alternatively be a patient programmer that allows a patient to communicate with the IMD 104. As another example, the EI 102 may be an intermediary device that communicates with the IMD 104 and also communicates with a local or remote device programmer, with servers or other peers over a data network, and with other external devices.

The IMD 104 may also be of various forms. For example, the IMD 104 may be a defibrillator, a pacemaker, a neurostimulator, a physiological data collector, substance delivery device, or various combinations of such devices. One or more embodiments of the IMD 104 may include leads 106 and corresponding electrodes 108. The electrodes 108 may interface electrically and/or mechanically with the tissue of the patient in order to deliver stimulation and/or to measure electrical, mechanical, and/or chemical activity of the surrounding tissue. In other instances, the catheters or other substance delivery elements may be present in place of or in addition to leads 106 and electrodes 108.

The pathway of the telemetry link between the EI 102 and the IMD 104 may be less than ideal. Noise and interference may be present, both in the communication band used for transferring the data as well as out of the band. Furthermore, depending upon the distance between the EI 102 and the IMD 104, there may be obstructions present to attenuate the communications signals. The noise and interference as well as any obstructions that are present may change. Thus, modulation parameter settings being employed by the EI 102 and the IMD 104 may adapt to compensate for difficult conditions or to capitalize upon improved conditions.

Examples of modulation parameter settings include modulation type settings and modulation symbol rate settings. Modulation type settings may specify which modulation type to use, such as amplitude-shift keying (ASK), frequency-shift keying (FSK), quadrature amplitude modulation (QAM), phase-shift keying (PSK), binary phase-shift keying (BPSK), differential binary phase-shift keying (DBPSK), quadrature phase-shift keying (QPSK), and differential quadrature phase-shift keying (DQPSK). Modulation symbol rate settings may specify the particular symbol rate to use, examples of which may include 1 kilosymbol per second or less up to 300 kilosymbols or more per second.

Figure 2A:
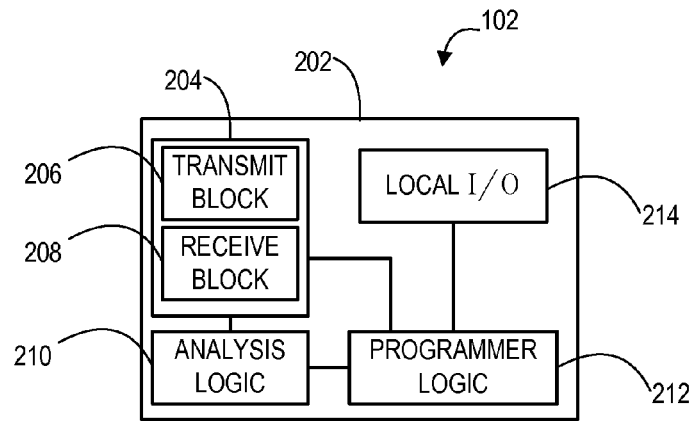
FIG. 2A shows a block diagram of the components of an illustrative embodiment of an external instrument.

FIG. 2A shows one example of the components of an EI 102. In this example, the EI 102 acts as a master to the communications session by performing an analysis of a quality metric for the telemetry link and then initiating the change of modulation parameter settings when appropriate to adapt.

The EI 102 includes communication circuitry such as a transceiver 204. This transceiver 204 includes a transmit block 206 and a receive block 208. The transceiver 204 has the ability to change modulation parameter settings. So, for instance, the transceiver 204 may have the ability to switch from one modulation type to another modulation type and/or switch from one symbol rate to another symbol rate. Furthermore, in some embodiments, the change of modulation parameter settings may change for both the transmit block 206 and the receive block 208 so that both the uplink and the downlink are adapted in the same manner, while in other embodiments a given change may apply to only the transmit block 206 or only the receive block 208 so that the uplink and the downlink may be individually adapted. Where a modulation parameter setting of only one block is changed, only the complementary block of the IMD 104, discussed in more detail below, is changed. So, for instance, if only the transmit block 206 changes a modulation parameter setting, then only the receive block of the IMD 104 changes the modulation parameter setting and makes the same change as the transmit block 206.

A programmer logic block 212 is included to perform the programming functions of the EI 102, such as to submit instructions and other data to the IMD 104 and to control other operations of the EI 102 including interfacing with a user to exchange instructions and other information. The programming logic block 212 may communicate with a user and/or other peripheral devices through a local input/output (I/O) block 214. The I/O block 214 may provide functions such as displaying a graphical user interface on a screen, receiving user inputs through user input devices such as a touchscreen, keyboard, mouse, and the like.

The programming logic block 212 may communicate with the transmit block 206 and receive block 208 to exchange the information to be transmitted to or received from the IMD 104. The programming logic block 212 may also communicate with the transmit block 206 and the receive block 208 to specify the modulation parameter settings that are to be used at any given time.

An analysis logic block 210 may also be included to analyze a quality metric of the telemetry link between the EI 102 and the IMD 104. The analysis logic block 210 may receive communication signal values from the transceiver 204, and particularly the receive block 208. The analysis logic block 210 then performs an analysis of the communication signal values to determine the quality metric and then to determine what change, if any, to a modulation parameter setting should be done.

For example, the analysis logic block 210 may measure a received signal strength indicator (RSSI) of the receive block 208 during active and idle communication frames to determine a total power of the received signal in each situation. Active communication frames and idle communication frames are discussed in more detail below with reference to FIGS. 2B and 4A-4C. From the RSSI, in some embodiments the analysis logic block 210 may proceed with the RSSI from an active frame as the quality metric. As alternatives, other embodiments may compute a signal-to-noise ratio, which may also be referred so as a signal-to-noise-and-interference ratio (SNIR), from the RSSI taken during an active frame and from additional RSSI measurements taken during idle frames, where the SNIR is then used as a quality metric to determine if a change to modulation parameter settings is appropriate.

The transmit block 206 and receive block 208 may use the same carrier frequency in various embodiments, which would also be the same carrier frequency in use by transmit and receive blocks of the IMD 104 which are discussed below. In that case the SNIR computation by only one of the two devices, such as the EI 102, may be a good estimate of the SNIR that both the EI 102 and the IMD 104 are experiencing. In that case, measurements at only one device, such as the EI 102, may be adequate to make decisions about link quality being experienced by both devices such that the one device performing the analysis may unilaterally decide if and when to adapt the modulation parameter settings.

Figure 2B:
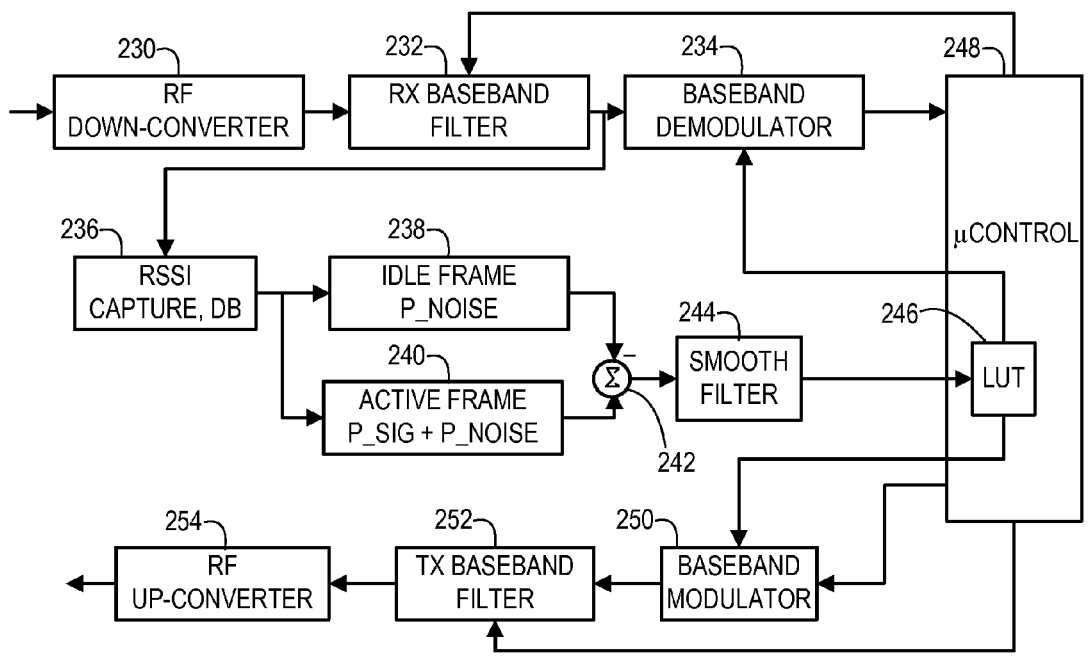
FIG. 2B shows a control diagram of the communication related components of the illustrative embodiment of the external instrument.

As shown in FIG. 2B, this illustrative embodiment of the EI 102 includes various functional blocks that coincide with those shown in FIG. 2A. For instance, the EI 102 of this example includes a radio frequency (RF) down-converter 230, receiver baseband filter 232, and a baseband demodulator 234, which together form one example of the receive block 208. Likewise, the EI 102 of this example includes a baseband modulator 250, transmitter baseband filter 252, and an RF up-converter 254 that together form one example of the transmit block 206.

The EI 102 also includes an RSSI capture block 236, an idle frame noise power block 238, an active frame signal plus noise power block 240, a summation node 242, a smooth filter 244, and a look-up table (LUT) 246. Together, these features form one example of the analysis logic 210. The RSSI capture block 236 monitors the signal strength of an output of the receiver baseband filter 232. At this point, the information being carried over the telemetry link, if any, has been extracted from the RF carrier at the RF down-converter 230 and the resulting baseband signal has been filtered at the baseband filter 232 to reduce the in-band noise and interference. The RSSI capture block 236 of this example may also convert the linear value to a logarithmic value, i.e., decibels.

For embodiments where the RSSI itself is the quality metric, then the RSSI value of the RSSI capture block 236 from an active frame may be referenced directly into the LUT 246 to find the modulation parameter settings that are appropriate for the current RSSI value. This look-up may use the linear RSSI value or the logarithmic value depending upon which is stored in the LUT 246.

For embodiments where the SNIR is the quality metric, then the RSSI of an idle frame is stored at the block 238 while the RSSI of an active frame is stored at the block 240. The logarithmic RSSI value of the block 238 is then subtracted from the logarithmic RSSI value of the block 240 at the summation node 242 to produce an SNIR value. The smooth filter 244 may then apply low pass filtering to remove excessive noise and the resulting SNIR value is found within the LUT 246 to find what modulation parameter settings are currently appropriate.

The LUT 246, an example of which is discussed in more detail below with reference to FIG. 7, associates one or more modulation parameter settings to ranges of RSSI values and/or SNIR values. Thus, when the analysis logic 210 finds that modulation parameter settings associated with the current RSSI, SNIR, or other link quality metric are different than those currently being used by the transceiver 204, then a parameter setting of the transceiver is changed to the value found in the LUT 246. The LUT 246 may be reprogrammable to adapt the values of parameter settings for given situations, and the LUT 246 may be contained within a microcontroller 248 to facilitate such reprogramming.

The microcontroller 248 receives the incoming data from the IMD 104 that is output by the baseband demodulator 234 and also provides data destined for the IMD 104 to the baseband modulator 250. The microcontroller 248 may be used to implement all or a part of the programmer logic block 212 as well as perform one or more functions of the analysis logic block 210, such as to communicate the new modulation parameter setting to the transmit block 206 and/or receive block 208. Furthermore, the microcontroller 248 may also alter settings of the baseband filters 232 and 252 when changing modulation parameter settings.

The functional blocks 236, 238, 240, 242, 244, and 246 may be implemented in various forms such as hardwired digital logic, one or more application specific integrated circuits, in firmware, and/or as programming for a general purpose programmable processor. Furthermore, these blocks may be an integrated function of the microcontroller 248 or may be provided by one or more separate physical components.

The logic of these blocks that determines the quality of the telemetry link, determines which modulation parameter setting to use at a given time, and that submits the instruction to change settings to the transceiver 204 may be stored on a computer readable medium. Computer readable media may be of various forms, such as electronic, magnetic, or optical storage devices.

Figure 3A:
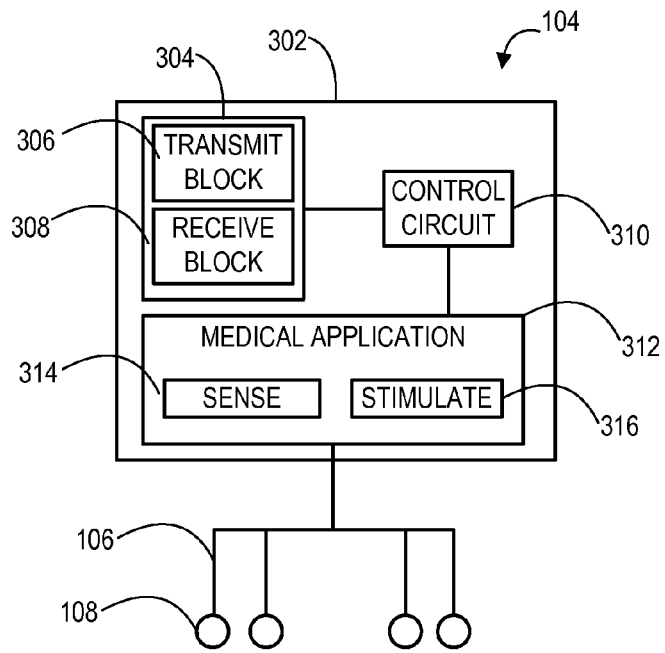
FIG. 3A shows a block diagram of the components of an illustrative embodiment of an implantable medical device.

FIG. 3A shows one example of the components of an IMD 104. In this example, the IMD 104 acts as a subordinate to the master, or EI 102, of the communications session. In this example, the IMD 104 listens for requests from the EI 102 to change modulation parameter settings and then implements those requests when they are received. However, it will be appreciated that the roles could be reversed in other embodiments, whereby the IMD 104 becomes the master and the EI 102 is the subordinate. In that case, the analysis logic 210 discussed above in relation to FIG. 2A may be implemented at the IMD 104.

The IMD 104 includes communication circuitry such as a transceiver 304. This transceiver 304 includes a transmit block 306 and a receive block 308. The transceiver 304 has the ability to change modulation parameter settings. So, as with the transceiver 204 of the EI 102, the transceiver 304 may have the ability to switch from one modulation type to another modulation type and/or switch from one symbol rate to another symbol rate. Furthermore, in some embodiments, the change of modulation parameter settings may change for both the transmit block 306 and the receive block 308 so that both the uplink and the downlink are adapted in the same manner, while in other embodiments a given change may apply to only the transmit block 306 or only the receive block 308 so that the uplink and the downlink may be individually adapted. The transmit block 206 of the EI 102 and the receive block 308 of the IMD 104 utilize matching modulation parameter settings for type, rate, and so forth while the transmit block 306 of the IMD 104 and the receive block 208 of the EI 102 utilize matching modulation parameter settings.

In the example shown in FIG. 3A, the IMD 104 includes control circuitry 310 that communicates with the transceiver 304 to receive incoming data from the EI 102 and also to provide outgoing data destined for the EI 102. The control circuitry 310 also communicates with medical application circuitry 312 for various purposes. For instance, such communication may allow for configuring medial task parameter settings of the medical application circuitry based on operational instructions received from the EI 102. Such communications may also allow for collection and reporting of physiological or other data generated by the medical application circuitry 312 in accordance with operational instructions received from the EI 102.

The medical application circuitry 312 may include a sensing block 314 and/or a stimulation block 316. The sensing and/or stimulation activities may be implemented using therapy delivery elements such as electrical leads 106 and corresponding electrodes 108. The leads 106 may extend to various parts of a patient's body 110 while the electrodes 108 may interact with the surrounding tissue to sense and/or stimulate. In another embodiment, stimulation block 316 may include, or may be replaced with, a delivery block for delivering a substance (e.g., a drug) to a patient, which may comprise a pump and the therapy delivery elements may comprise one or more catheters.

Figure 3B:
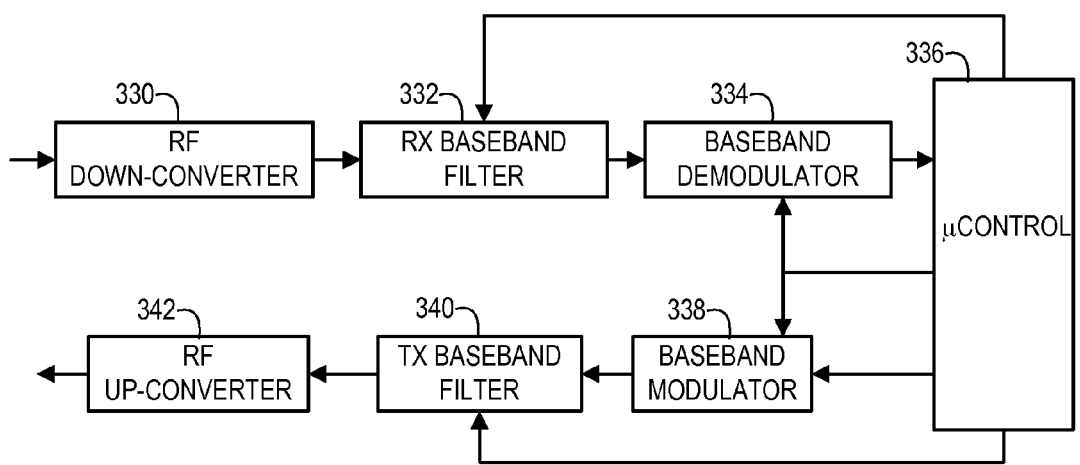
FIG. 3B shows a control diagram of the communication related components of the illustrative embodiment of the implantable medical device.

FIG. 3B shows an illustrative embodiment of the IMD 104 that includes various functional blocks that coincide with those shown in FIG. 3A. For instance, the IMD 104 of this example includes an RF down-converter 330, receiver baseband filter 332, and a baseband demodulator 334, which together form one example of the receive block 308. Likewise, the IMD 104 of this example includes a baseband modulator 338, transmitter baseband filter 340, and an RF up-converter 342 that together form one example of the transmit block 306.

A microcontroller 336 receives the incoming data from the EI 102 that is output by the baseband demodulator 334 and also provides data destined for the EI 102 to the baseband modulator 338. The microcontroller 336 may be used to implement all or a part of the control circuitry 310 as well as perform one or more functions of the medical application circuitry 312, such as to communicate the new modulation parameter setting to the transmit block 306 and/or receive block 308. Furthermore, the microcontroller 336 may also alter settings of the baseband filters 332 and 340 when changing modulation parameter settings.

The logic of the microcontroller 336 or other physical component that recognizes a request to change the modulation parameter setting at a given time and that submits the instruction to change settings to the transceiver 304 may also be stored on a computer readable medium.

While FIG. 3B shows an example of the IMD 104 as a subordinate to the EI 102, the roles may be reversed. In that case, the functional blocks 236, 238, 240, 242, 244, and 246 of the EI 102 shown in FIG. 2B may be included for the IMD 104. In that case the IMD 104 may communicate a request to change settings to the EI 102, and the microcontroller 248 of the EI 102 may recognize the request and then instruct the transmit block 206 and receive block 208 accordingly.

Figure 4A:
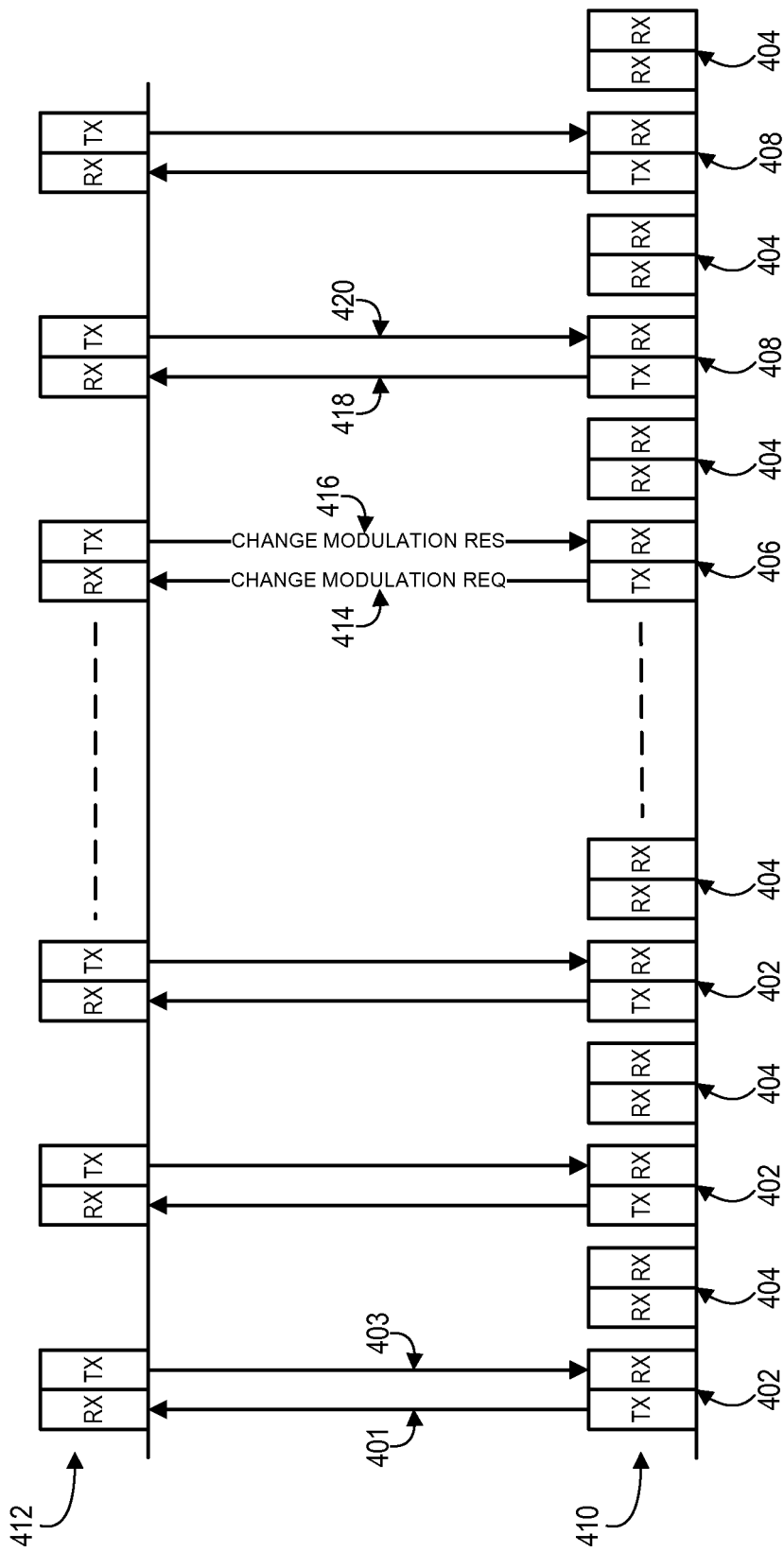
FIG. 4A shows a timeline of communication exchanges for a successful adaptation of a modulation parameter setting.

FIG. 4A shows a timeline of events where the EI 102 is acting as a master and determines that a change of modulation parameter settings is warranted. On this timeline, a row 410 indicates the actions of the EI 102 while a row 412 indicates the actions of the IMD 104. Active frames 402 include a transmission 401 by the EI 102 and a return transmission 403 by the IMD 104 while using initial modulation parameter settings. The EI 102 obtains an active frame RSSI while receiving. During idle frames 404, there is no transmission by either the EI 102 or the IMD 104, but the EI 102 continues to listen for noise and interference and obtain a corresponding idle frame RSSI while using an initial set of modulation parameter settings. In this example, the EI 102 and IMD 104 are configured to transmit during certain time periods and receive during others such that the EI 102 expects to receive at certain time slot within certain time frames while the IMD 104 expects to receive at another time slot during the same time frames. It will be appreciated that different configurations for transmitting and receiving are also applicable such as where the EI 102 transmits in one time frame while the IMD 104 transmits in an entirely different time frame. In such cases, the EI 102 and IMD 104 may are aware of when to expect to receive a transmission by the other device.

At some point in time, the master or EI 102 in this case determines that the link quality is such that a modulation parameter setting should be changed. The link quality could be based on RSSI alone, SNIR, or other metrics. Thus, at an active frame 406, the EI 102 sends a transmission 414 that requests that the IMD 104 make a change to one or more modulation parameter settings. The IMD 104 then sends a response transmission 416 to acknowledge the request.

At the next active frame 408, the EI 102 sends a transmission 418 while using an updated modulation parameter setting. The IMD 104 successfully receives the transmission 418 and then sends a return transmission 420 using an updated modulation parameter setting. Communication then proceeds.

In this example, the modulation parameter setting has changed for the uplink and the downlink. The updated modulation parameter setting may be the same for both or may be different. Furthermore, it will be appreciated that either the request for a change and the implementation of the requested change could have been for only the uplink or for only the downlink.

Figure 4B:
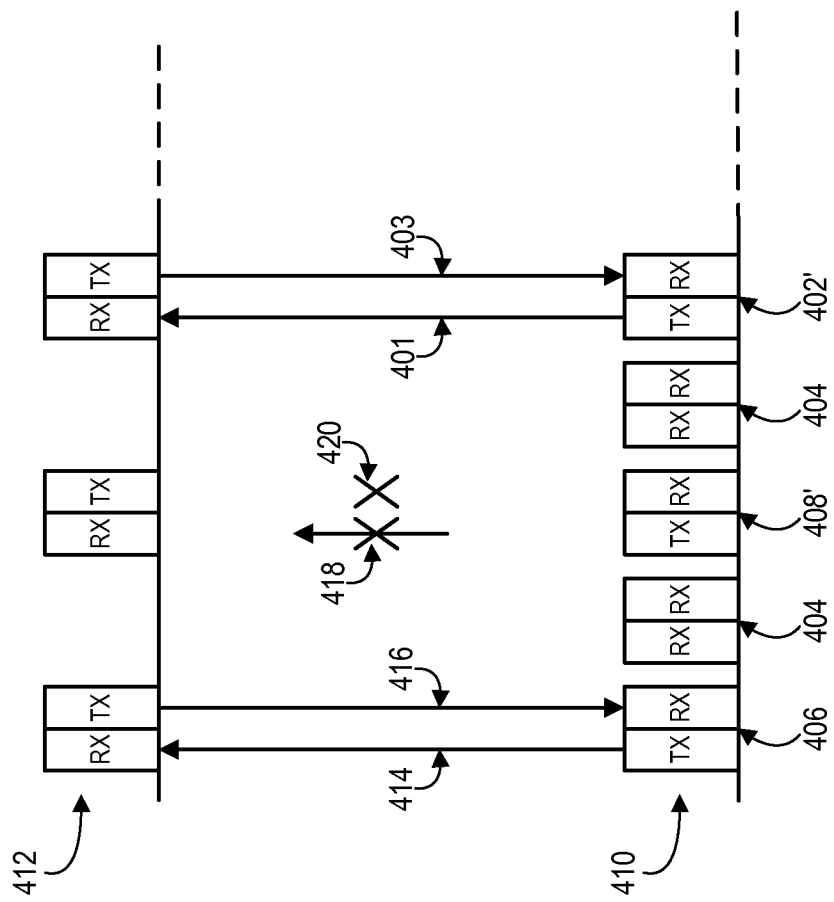
FIG. 4B shows a timeline of communication exchanges for one example of a recovery following an unsuccessful adaptation of a modulation parameter setting.

FIG. 4B shows one example where a recovery occurs when an attempt at adapting modulation parameter settings has failed. This timeline begins at the active frame 406 where the EI 102 transmits the request to change the modulation parameter setting via the transmission 414. The IMD 104 then responds via the transmission 416 to acknowledge the request. At the next active frame 408', the EI 102 then sends a transmission 418 using the adapted modulation parameter setting. However, as indicated by the X, this transmission 418 is not received by the IMD 104.

The IMD 104 is aware that the transmission 418 has not been received. However, the EI 102 is not aware of this. In this particular example, the IMD 104 may merely not transmit during the second time slot of this active frame 408' such that the EI 102 fails to receive a response as indicated by the X 420. At this point, the EI 102 knows that a problem has occurred, either due to the IMD 104 not receiving the transmission 418 and thus not transmitting at the X 420, or by the EI 102 not receiving whatever may have been transmitted by the IMD 104.

The EI 102 may then assume that the IMD 104 may not have received the transmission 418 and will recover by using the modulation parameter setting that was known to be working prior to the attempted change. Thus, the EI 102 may proceed to send a transmission 401 at the next active frame 402' that uses the modulation parameter setting that was known to be working prior to the attempted change. In this particular example, the IMD 104 did switch back to the modulation parameter setting that was known to be working prior to the attempted change since the IMD 104 was aware of the problem. Thus, the IMD 104 receives the transmission 401 and responds with the transmission 403 by also using the modulation parameter setting that was known to be working prior to the attempted change.

Figure 4C:
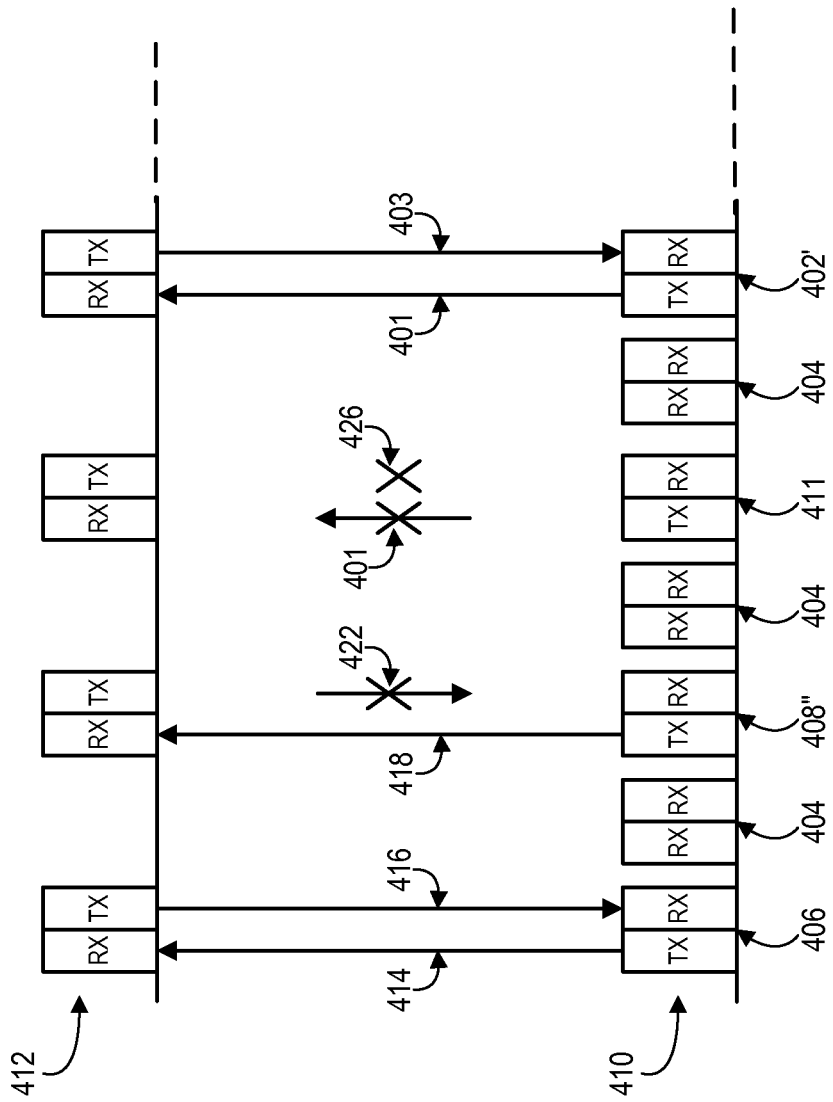
FIG. 4C shows a timeline of communication exchanges for another example of a recovery following an unsuccessful adaptation of a modulation parameter setting.

FIG. 4C shows another example where a recovery occurs when an attempt at adapting modulation parameter settings has failed. This timeline begins at the active frame 406 where the EI 102 transmits the request to change the modulation parameter setting via the transmission 414. The IMD 104 then responds via the transmission 416 to acknowledge the request. At the next active frame 408", the EI 102 then sends a transmission 418 using the adapted modulation parameter setting. This transmission 418 is successfully received by the IMD 104.

The IMD 104 then responds with a transmission 422 that is sent by using the adapted modulation parameter setting, considering that in this example the requested change is applicable to both the uplink and downlink. However, the transmission 422 is not received by the EI 102 as indicated by the X. The EI 102 is aware that the transmission 422 has not been received. However, the IMD 104 is not aware of this.

The EI 102 may then assume that the IMD 104 may not have received the transmission 418 which caused the transmission 422 to not be sent by the IMD 104 and will recover by using the modulation parameter setting that was known to be working prior to the attempted change, as was the case in FIG. 4B. Thus, the EI 102 may proceed to send a transmission 401 at the next active frame 411 that uses the modulation parameter setting that was known to be working prior to the attempted change. In this particular example, the IMD 104 does not realize that there is a problem with the adapted modulation parameter setting and is attempting to receive by using the adapted modulation parameter setting. As a result, the transmission 401 from the EI 102 is not received, as is indicated by the X.

In this particular example, the IMD 104 may merely not transmit during the second time slot of this active frame 411 such that the EI 102 fails to receive a response as indicated by the X 426. At this point, the EI 102 may conclude that a problem has occurred due to the IMD 104 attempting to receive by using the adapted modulation parameter setting. However, under this recovery scheme, the IMD 104 may be expected to receive two consecutive transmissions using the adapted modulation parameter setting or else revert back to the previous modulation parameter setting.

At the next active frame 402', the EI 102 then sends the transmission 401 again using the modulation parameter setting that was known to be working prior to the attempted change. Because the IMD 104 failed to receive two consecutive transmissions from the EI 102 using the adapted modulation parameter setting, the IMD 104 has reverted back to the previous modulation parameter setting and successfully receives the transmission 401. The IMD 104 then sends the transmission 403 to the EI 102 using the previous modulation parameter setting which is also now being used by the EI 102, and the transmission 403 is successfully received.

Figure 5A:
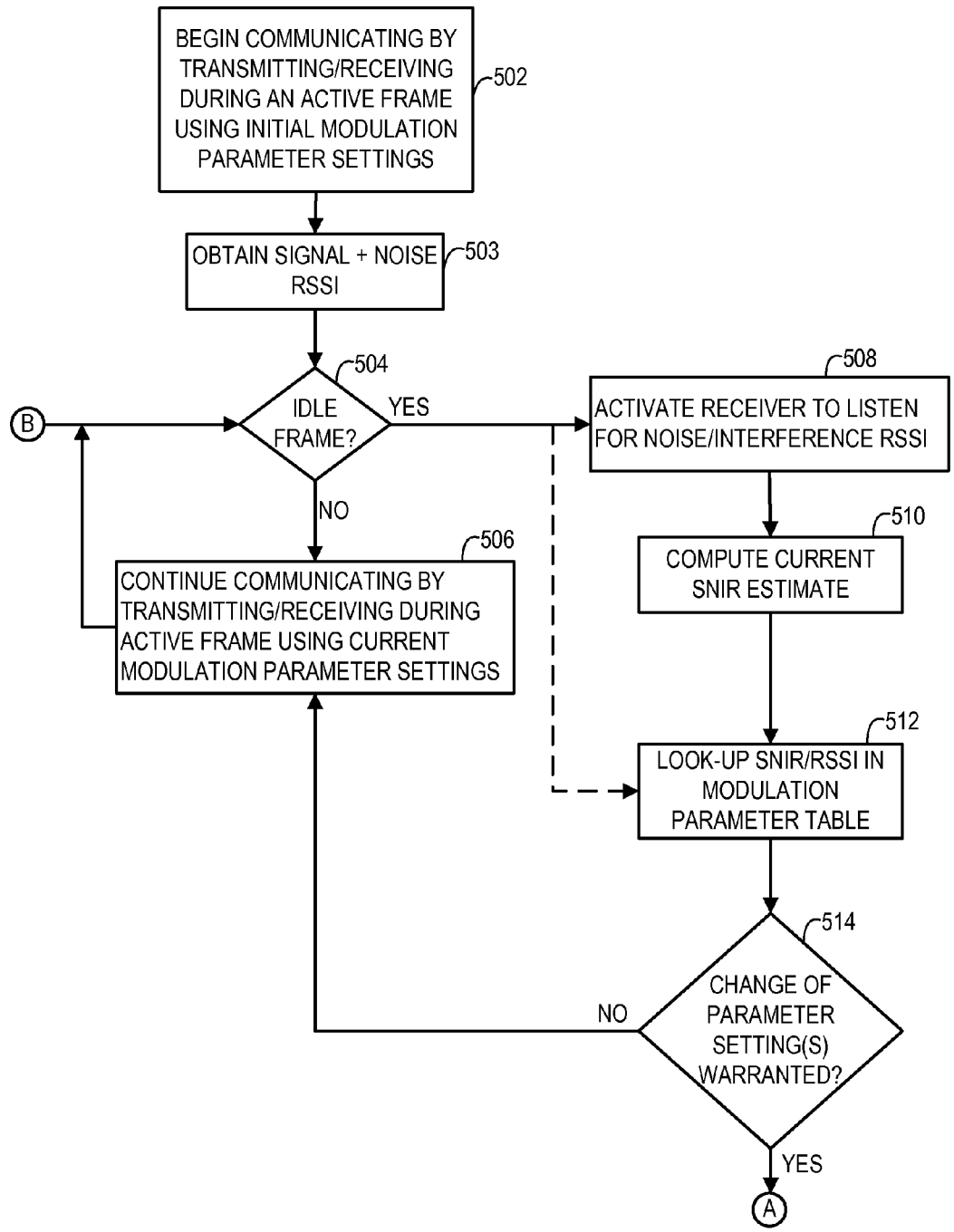
FIG. 5A shows a first portion of one example of a set of logical operations that may be performed by a device acting as a master for the communications.
Figure 5B:
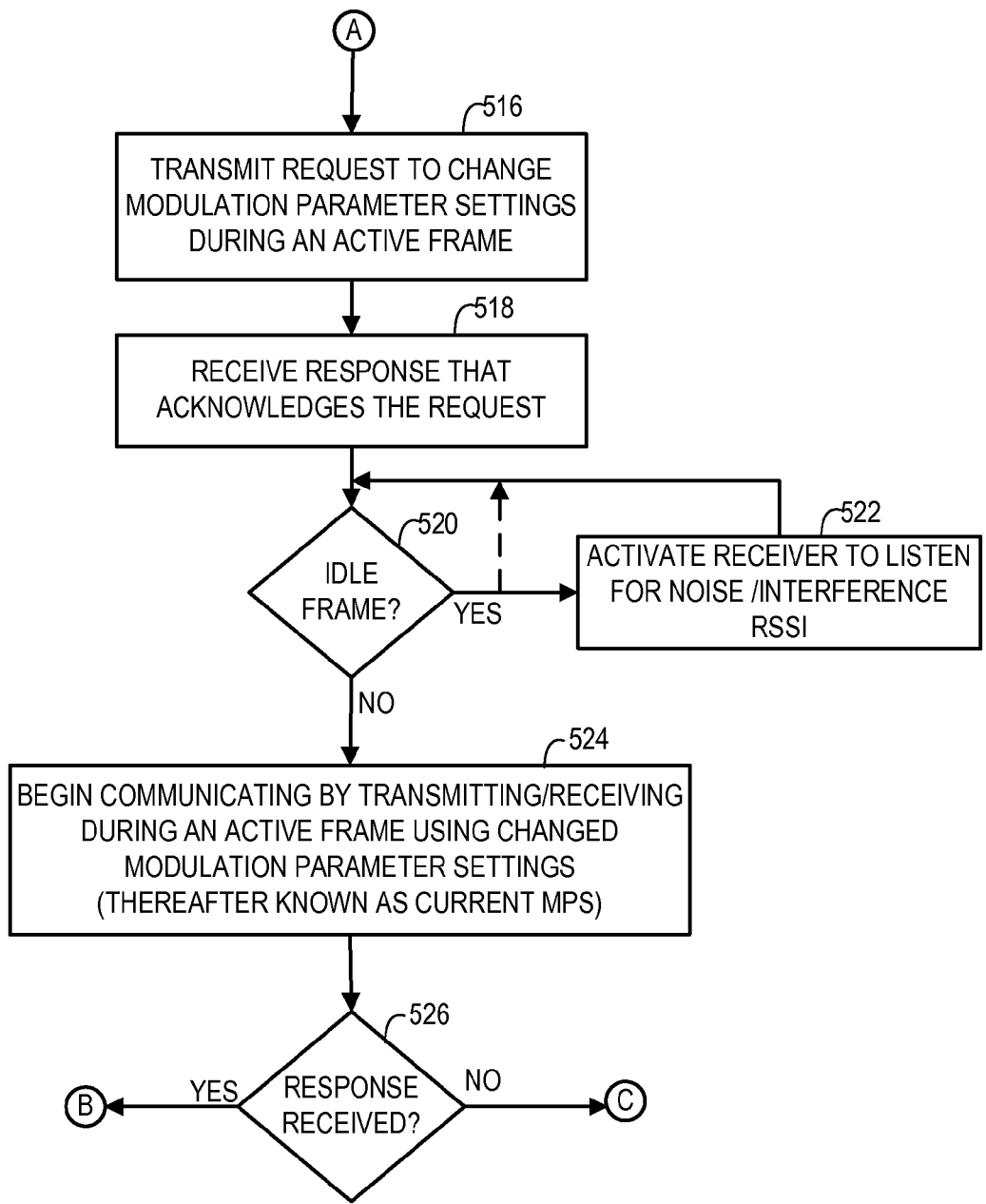
FIG. 5B shows a second portion of one example of a set of logical operations that may be performed by a device acting as a master for the communications.
Figure 5C:
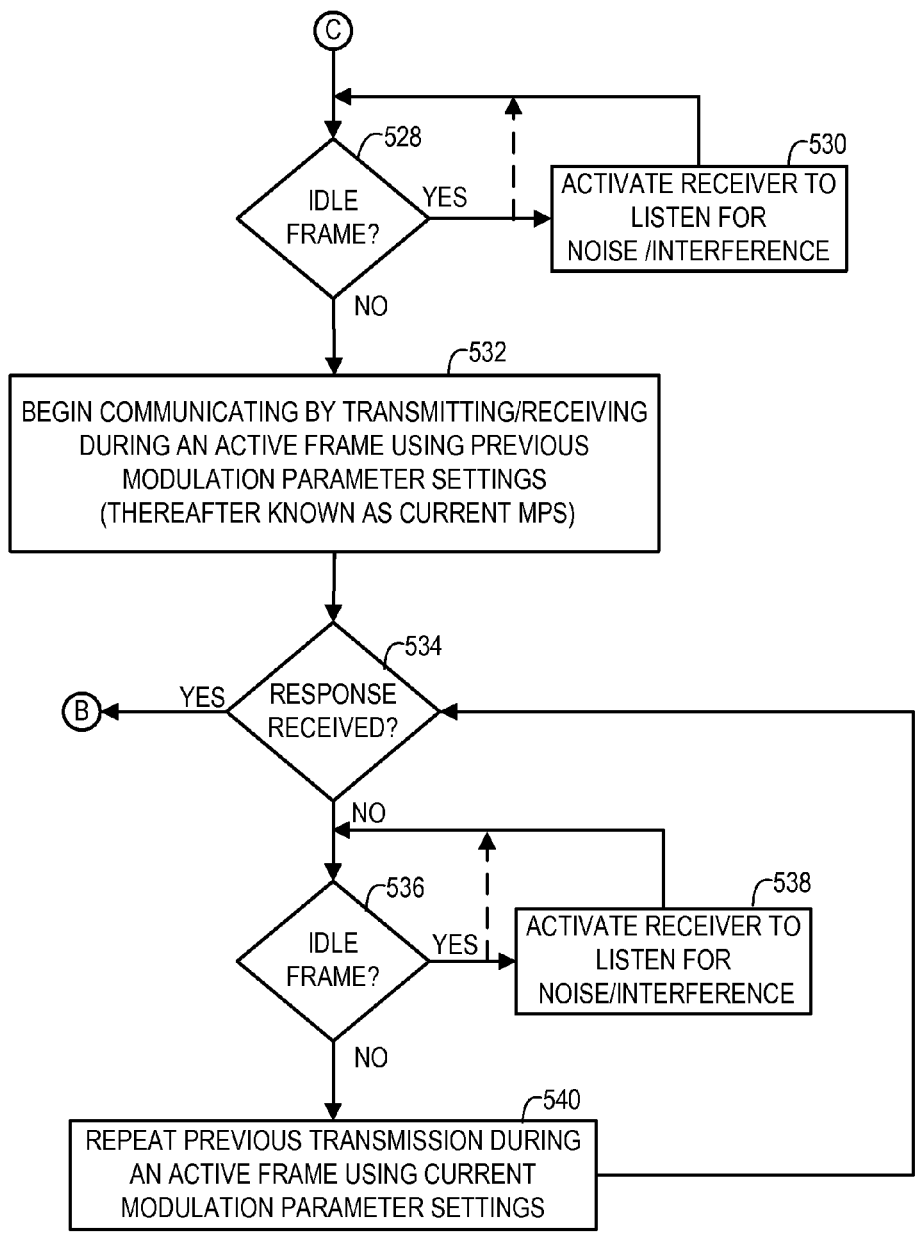
FIG. 5C shows a third portion of one example of a set of logical operations that may be performed by a device acting as a master for the communications.

FIGS. 5A-5C show one example of logical operations that may be performed by the master, in this case the EI 102, in correspondence with the scenarios of FIGS. 4A-4C. The EI 102 begins communicating by transmitting and then receiving during an active frame using the initial modulation parameter settings at a communication operation 502. The EI 102 obtains the active frame RSSI at a signal operation 503. At a query operation 504, the EI 102 detects the time for an idle frame. Upon the time for an idle frame occurring, for embodiments where the SNIR will be used as the quality metric, then the EI 102 activates the receiver block 208 to listen for the primarily in-band noise and interference at a reception operation 508. For embodiments where the RSSI alone will be used as the quality metric, then operational flow skips to a look-up operation 512 as indicated by the phantom line.

Returning to the embodiment using the SNIR, the SNIR estimate is computed at the computation operation 510. The EI 102 then performs a look-up in the LUT 246 for the SNIR. In the alternate, the EI 102 looks up the RSSI in the LUT 246. The EI 102 then determines whether a modulation parameter setting should be changed at a query operation 514 by comparing the modulation parameter setting found in the LUT 246 to the modulation parameter setting currently in use.

When no modulation parameter setting change is needed, then the EI 102 continues communicating by transmitting and receiving during the next active frame using the current modulation parameter settings at a communication operation 506. Then the logical operations return to the query 504 to await another idle frame.

Where a modulation parameter setting does need to be changed per the query operation 514, processing continues to FIG. 5B where the EI 102 transmits a request to change the modulation parameter setting during the next active frame at a transmission operation 516. During this active frame, the EI 102 then receives the response from the IMD 104 at a reception operation 518. At the next idle frame per a query operation 520, the EI 102 then uses the receiver block 208 to again listen for the noise and interference and thus obtain another idle frame RSSI at the reception operation 522. Alternatively, such as where the RSSI alone is the quality metric, the operational flow remains at the query operation 520 until the next active frame arrives.

At the next active frame, the EI 102 then begins communicating by transmitting and then receiving during the active frame by using the changed modulation parameter settings at a communication operation 524. For purposes of following the sequence of logical operations, the changed modulation parameter settings are now considered to be the current modulation parameter settings. At a query operation 526, the EI 102 then determines whether a response from the IMD 104 was received.

Where a response from the IMD 104 has been received, then operational flow returns to the query operation 504 of FIG. 5A to again detect the next idle frame. Where a response from the IMD 104 is not received, then the EI 102 awaits the idle frame 528 of FIG. 5C, and then activates the receive block 208 to listen for idle frame RSSI value at receive operation 530, or alternatively awaits the conclusion of the idle frame such as where only active frame RSSI values are being considered.

At the next active frame, the EI 102 begins communicating by transmitting and receiving using the previous modulation parameter settings, which are referred to as the current modulation parameter settings at a communication operation 532. The EI 102 detects whether a response has been received to the attempt at transmitting and receiving using the current modulation parameters at a query operation 534. If the response is received, then operational flow proceeds to the communication operation 506 of FIG. 5A. At this point, the recovery sequence shown in FIG. 4B has been achieved.

Returning to the query operation 534, if the response has not been received, then at a query operation 536, the EI 102 again detects an idle frame. During the idle frame, the EI 102 then activates the receive block 208 to listen for the idle frame RSSI value, or alternatively awaits the conclusion of the idle frame such as where only active frame RSSI values are being considered. Upon the next active frame, the EI 102 then repeats the previous transmission 540 using the current modulation parameter settings, which are those that are known to have worked prior to the attempted change, at the communication operation 540. Operational flow then returns to the query operation 534 to again detect whether a response has been received. This repeats until a response is received, and at this point, the recovery sequence shown in FIG. 4C has been achieved.

Figure 6A:
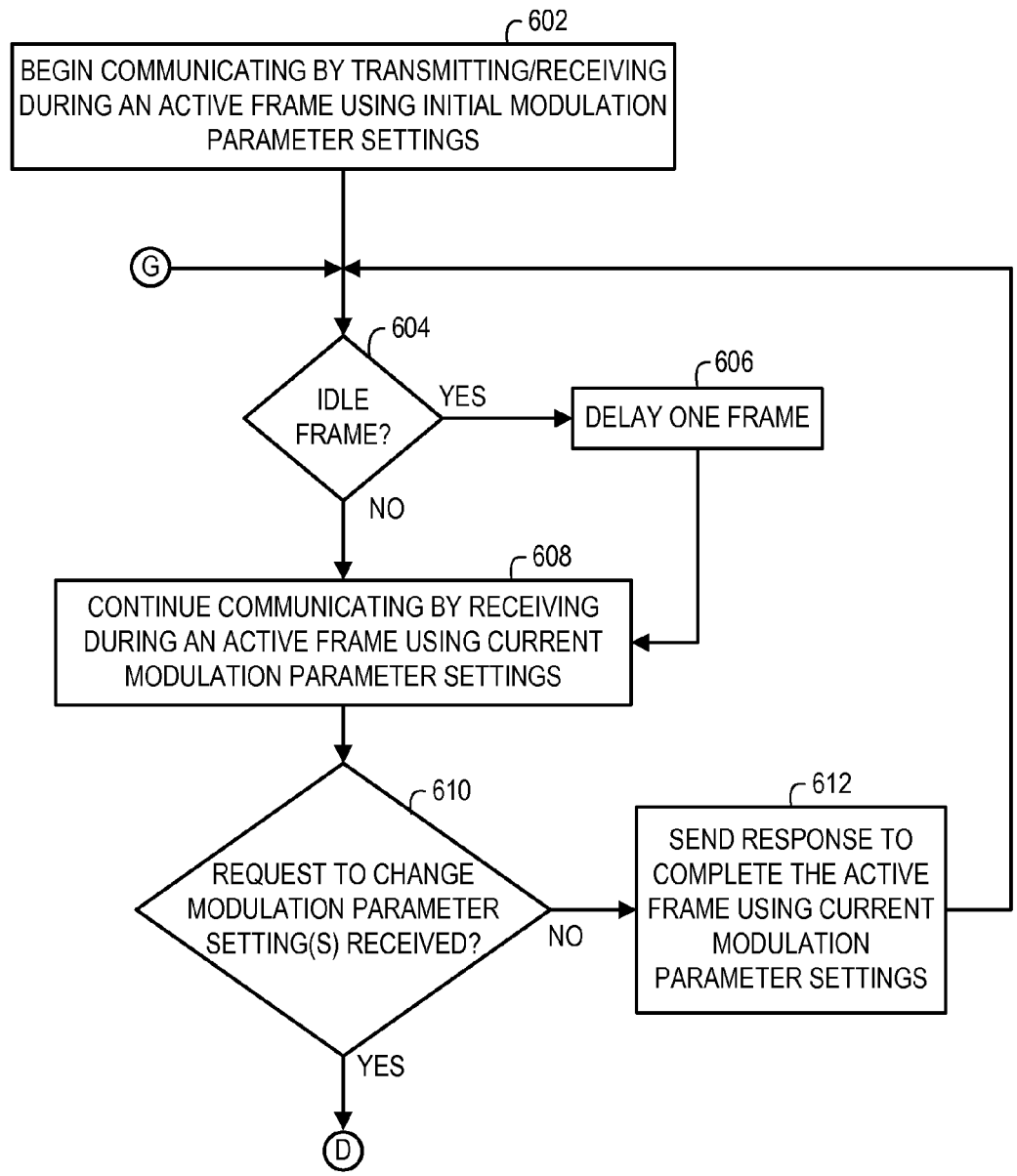
FIG. 6A shows a first portion of one example of a set of logical operations that may be performed by a device acting as a subordinate for the communications.
Figure 6B:
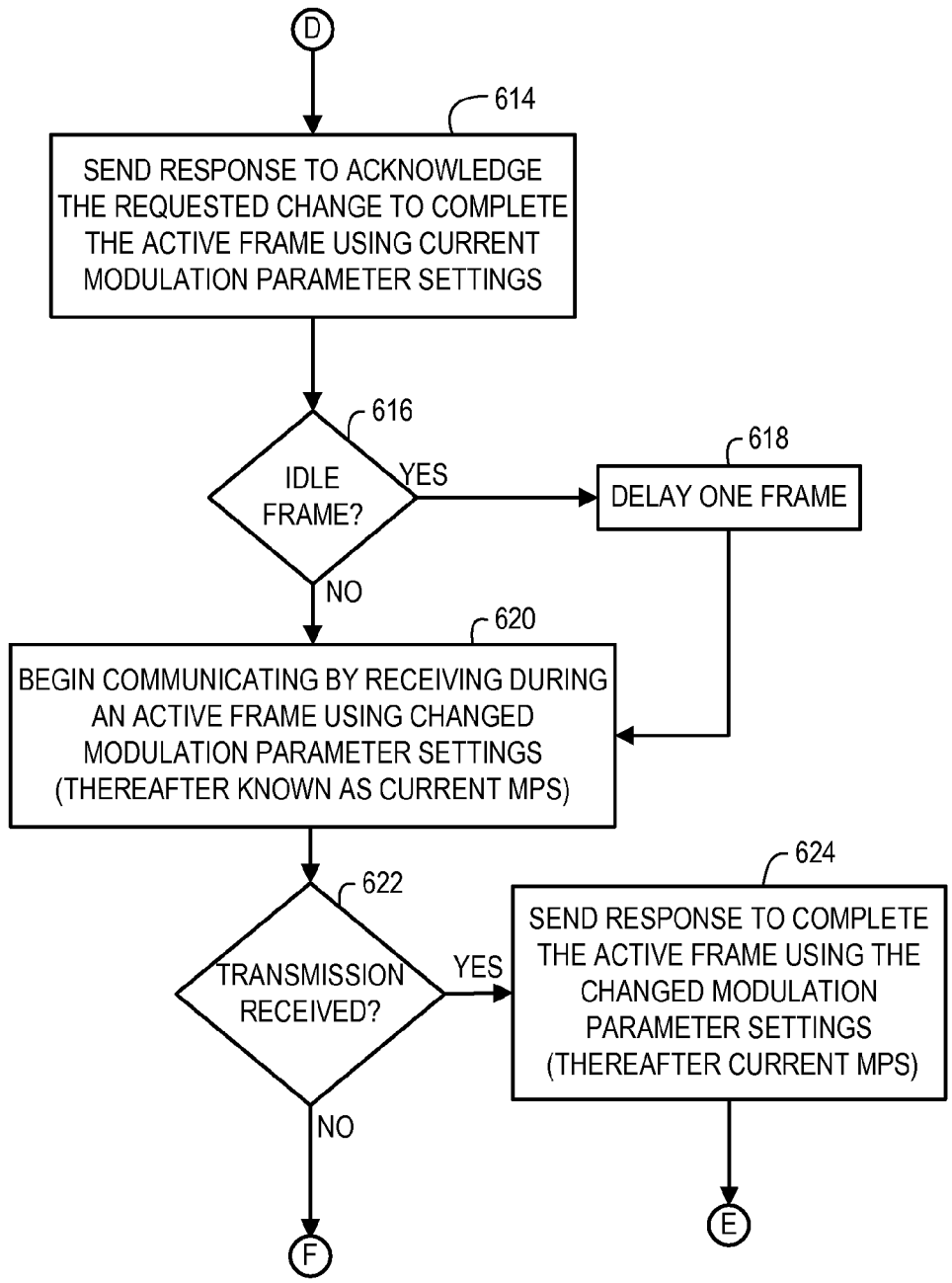
FIG. 6B shows a second portion of one example of a set of logical operations that may be performed by a device acting as a subordinate for the communications.
Figure 6C:
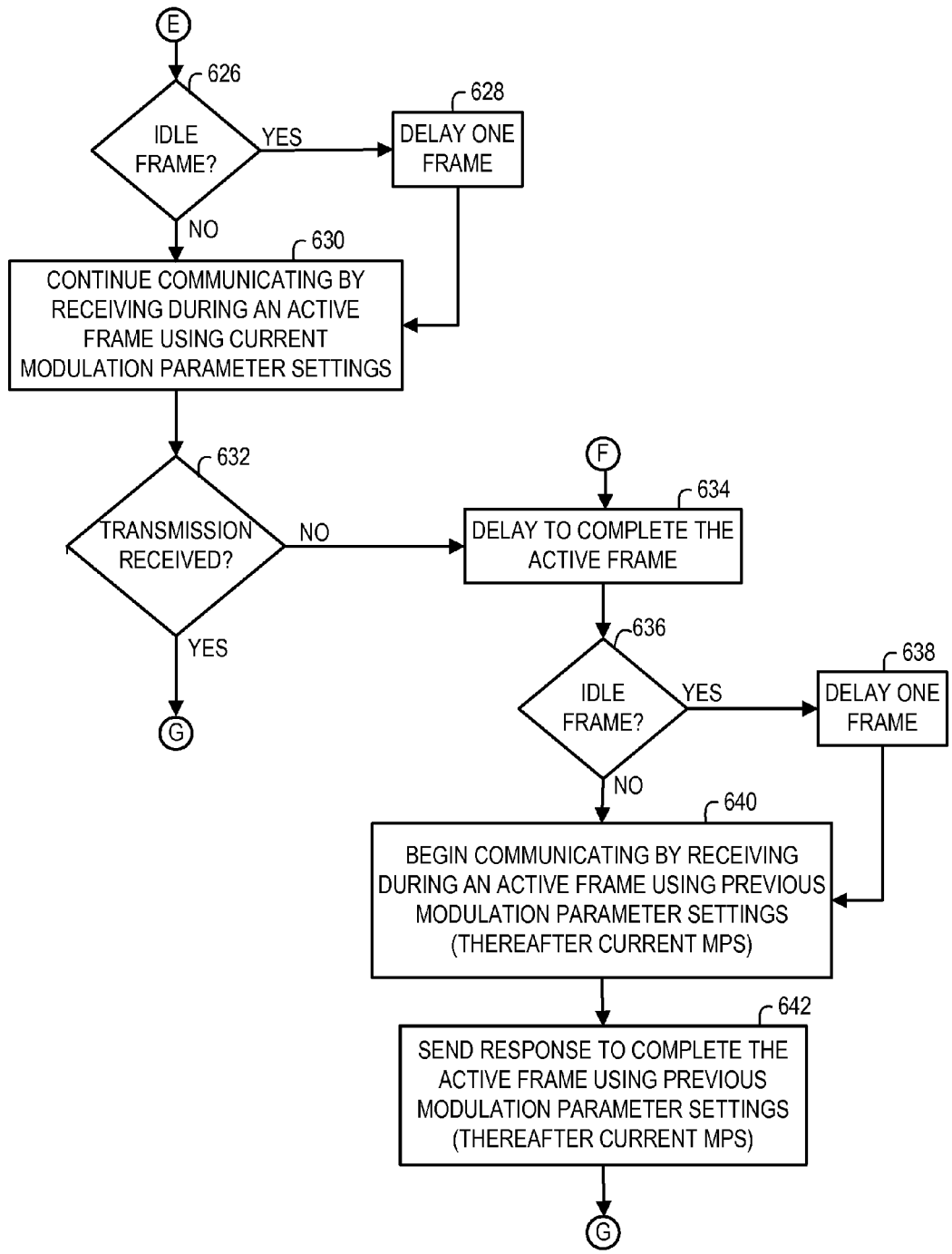
FIG. 6C shows a third portion of one example of a set of logical operations that may be performed by a device acting as a subordinate for the communications.

FIGS. 6A-6C show one example of logical operations that may be performed by the subordinate, in this case the IMD 104, in correspondence with the scenarios of FIGS. 4A-4C. The IMD 104 begins communicating by receiving and then transmitting during an active frame while using the initial modulation parameter settings at a communication operation 602. At a query operation 604, the IMD 104 then detects whether the time for an idle frame has occurred. If so, then the IMD 104 delays for the number of frames until the next active frame at a delay operation 606. In the example shown, the active frame is every other frame and so the IMD 104 delays for one idle frame.

After the idle frame has ended, then the IMD 104 continues communicating by receiving during the active frame while using the current modulation parameter settings at a communication operation 608. The IMD 104 then detects at a query operation 610 whether a request to change modulation parameter settings has been received. If not, then the IMD 104 sends a response back to the EI 102 to complete the active frame while using the current modulation parameter settings at a response operation 612, and operational flow returns to the query operation 604 to detect the next idle frame.

Where a request to change modulation parameter settings is received, processing proceeds to FIG. 6B where the IMD 104 then sends a response back to the EI 102 that acknowledges the requested change to complete the active frame while using the current modulation parameter settings at a response operation 614. At a query operation 616, the IMD 104 then detects whether the time for an idle frame has occurred. If so, then the IMD 104 delays for the number of frames until the next active frame at a delay operation 618.

After the idle frame has ended, then the IMD 104 continues communicating by receiving during the active frame while using the changed modulation parameter settings at a communication operation 620. For purposes of following the sequence of logical operations, the changed modulation parameter settings are now considered to be the current modulation parameter settings when referring to receiving transmissions. At a query operation 622, the IMD 104 detects whether a transmission has been received during this active frame. If so, then the IMD 104 sends a response to complete the active frame while using the changed modulation parameter settings, which are now referred to as the current modulation parameter settings, at a response operation 624.

After sending the response at the response operation 624, then the IMD 104 detects whether an idle frame is occurring at a query operation 626 of FIG. 6C. Upon reaching an idle frame, then the IMD 104 delays at a delay operation 628 until the idle frame ends and then proceeds to a receiving operation 630. If no idle frame is occurring, then operational flow proceeds directly to the receiving operation 630. At the receiving operation 630, the IMD attempts to receive during an active frame using the current modulation parameters. A query operation 632 then detects whether a transmission has been received.

In relation to FIG. 4C, operation 632 is detecting whether the consecutively successful reception using the adapted modulation parameter setting has occurred. If reception has occurred, then operational flow returns to the query operation 604 of FIG. 6A and operational flow continues where the adapted modulation parameter setting continues to be used until time for another change. If reception has not occurred, this is indicative of the response that was sent at the response operation 624 not being received by the EI 102.

At this point, the IMD 104 may merely delay without transmitting to complete the current active frame at a delay operation 634. At a query operation 636, the IMD 104 then detects whether an idle frame is occurring. Upon reaching an idle frame, then the IMD 104 delays until the idle frame ends at a delay operation 638 and then proceeds to a receiving operation 640. If no idle frame is occurring, then operational flow proceeds directly to the receiving operation 640.

At the next active frame, the IMD 104 begins receiving using the modulation parameter settings that were known to be working prior to the change, which are now referred to as the current modulation parameter settings, at the receiving operation 640. As the IMD 104 successfully receives the transmission from the EI 102 at the receiving operation 640 by using the modulation parameter settings that are known to be working, then IMD 104 then sends a response using the working modulation parameter settings at a response operation 642. Operational flow then returns to the query operation 604 of FIG. 6A, and operational flow continues where the modulation parameter settings that are known to work continue to be used until time for another attempt at a change.

The logical operations such as those of FIGS. 5A-5C and 6A-6C may provide for one modulation parameter setting or multiple modulation parameter settings to be changed per iteration, and hence per analysis of the link quality. Furthermore, one iteration may result in one modulation parameter setting being changed while a subsequent iteration may result in a different modulation parameter setting being changed.

So, for instance, these operations may begin using a first initial modulation parameter such as modulation type and a second initial modulation parameter such as modulation rate, or vice versa. On one iteration, the first initial modulation parameter setting may be changed to a second modulation parameter setting, while the second initial modulation parameter setting remains unchanged. On another iteration, the second initial modulation parameter setting may be changed to a third modulation parameter setting while the second modulation parameter setting remains unchanged. On yet another iteration, the second modulation parameter setting may be changed to a fourth modulation parameter setting and so on. Furthermore, on any one of these iterations, more than one of the two or more modulation parameter settings may be changed, such as changing both the first initial modulation parameter setting and the second initial modulation parameter setting to the second and third modulation parameter settings, respectively.

FIG. 7 shows one example of an LUT 700 which may be used as the LUT 246 of FIG. 2B. This LUT 700 includes three columns of information, including a quality metric range 702, a modulation type 704, and a modulation symbol rate 706. The LUT 700 of this example also includes multiple pairs of rows 708 and 710, where the row 708 corresponds to an application 1 for which communications may occur at a given time while the row 710 corresponds to an application 2 for which communications may occur at a given time. For instance, the application 1 of row 708 may correspond to a lower priority application such as an exchange of stored physiological data while the application 2 of the row 710 may correspond to a higher priority application such as where the IMD 104 is receiving programming instructions being stored for future implementation or being implemented in real time.

The link quality column 702 may be specified as a range of RSSI values, as a range of SNIR values, or a range of other similar values that are representative of the quality of the wireless link. The modulation type column 704 may specify such modulation types as those discussed above such as various forms of shift keying, amplitude modulation, and so forth. The modulation symbol rate column 706 may specify particular rates to be used that may range from a minimal amount, such as 1 kilosymbol or less per second as an example, to a maximum amount, such as 300 kilosymbols or more per second as another example.

The link quality of column 702 may be specified as a set of ranges where each range is specified for each application. The modulation type 704 and/or modulation symbol rate 706 that is specified for a range represents what is most appropriate for that range and application.

For instance, when the communications pertain to application 1, and the link quality is in the range from A-B then the modulation type may be type X while the modulation symbol rate is K kilosymbols per second. When the application switches to application 2, and the link quality continues to range from A-B, then the modulation type may be maintained as type X, but the modulation symbol rate may be adapted from K to L.

As another example, when the communications pertain to application 1, and the link quality is in the range from B-C then the modulation type may be type Y while the modulation symbol rate is K kilosymbols per second. When the application switches to application 2, and the link quality continues to range from B-C, then the modulation symbol rate may be maintained as K kilosymbols per second, but the modulation type may be adapted from type Y to Z.

As another example, when the communications pertain to application 1, and the link quality is in the range from A-B then the modulation type may be type X while the modulation symbol rate is K kilosymbols per second. When the link quality changes to the range of B-C for application 1, then the symbol rate may be maintained as K kilosymbols per second but the modulation type is changed from type X to Y.

As another example, when the communications pertain to application 1, and the link quality is in the range from B-C then the modulation type may be type Y while the modulation symbol rate is K kilosymbols per second. When the link quality changes to that range from C-D for application 1, then the modulation type may be maintained as type Y, but the modulation symbol rate may be adapted from K to L.

While embodiments have been particularly shown and described, it will be understood by those skilled in the art that various other changes in the form and details may be made therein without departing from the spirit and scope of the invention.

What is claimed is:

1. A method of adapting communications between an implantable medical device and an external instrument, comprising:
   transferring communication signals using a first initial modulation parameter setting over a telemetry link between the implantable medical device and the external instrument;
   listening during a period of time when no communication signals are being transferred between the external device and the implantable medical device to obtain a signal strength reference;
   analyzing a quality metric of the communication signals that have been transferred, the analyzing comprising comparing the signal strength reference to a signal strength of the communication signals to obtain a signal-to-noise ratio for the telemetry link;
   selecting a second modulation parameter setting as a replacement for the first initial modulation parameter setting in response to the analysis, wherein selecting the second modulation parameter setting comprises performing a look-up of a link quality in a stored table that associates link quality to at least one modulation parameter setting; and
   transferring communication signals using the second modulation parameter setting over the telemetry link between the implantable medical device and the external instrument.

2. The method of claim 1, wherein transferring a communication signal using the first initial modulation parameter setting over the telemetry link comprises:
   transferring a first communication signal from the external instrument to the implantable medical device over the telemetry link; and
   transferring a second communication signal from the implantable medical device to the external instrument in response to the first communication signal over the telemetry link.

3. The method of claim 2, wherein analyzing the quality metric occurs at the external device by analyzing the second communication signal.

4. The method of claim 3, wherein analyzing the quality metric further comprises measuring by the external device a received signal strength.

5. The method of claim 2, wherein the first communication signal and the second communication signal are sent using a same carrier frequency.

6. The method of claim 1, wherein analyzing the quality metric comprises comparing by at least one of the external instrument or the implantable medical device the signal strength reference to the signal strength to obtain the signal-to-noise ratio for the telemetry link.

7. The method of claim 1, wherein the first initial modulation parameter setting comprises an initial modulation type and wherein the second modulation parameter setting comprises a first alternative modulation type.

8. The method of claim 7, wherein the initial modulation type comprises one of amplitude-shift keying (ASK), frequency-shift keying (FSK), quadrature amplitude modulation (QAM), phase-shift keying (PSK), binary phase-shift keying (BPSK), differential binary phase-shift keying (DBPSK), quadrature phase-shift keying (QPSK), and differential quadrature phase-shift keying (DQPSK).

9. The method of claim 8, wherein the first alternative modulation type comprises one of ASK, FSK, QAM, BPSK, DBPSK, QPSK, and DQPSK.

10. The method of claim 1, wherein the initial modulation parameter setting comprises an initial modulation symbol rate and wherein the second modulation parameter setting comprises a first alternative modulation symbol rate.

11. The method of claim 10, wherein the initial modulation symbol rate ranges from 1 to 300 kilosymbols per second.

12. The method of claim 11, wherein the first alternative modulation symbol rate ranges from 1 to 300 kilosymbols per second.

13. A method of adapting communications between an implantable medical device and an external instrument, comprising:
    transferring communication signals using a first initial modulation parameter setting over a telemetry link between the implantable medical device and the external instrument;
    listening during a period of time when no communication signals are being transferred between the external device and the implantable medical device to obtain a signal strength reference;
    analyzing a quality metric of the communication signals that have been transferred, the analyzing comprising comparing the signal strength reference to a signal strength of the communication signals to obtain a signal-to-noise ratio for the telemetry link;
    selecting a second modulation parameter setting as a replacement for the first initial modulation parameter setting in response to the analysis; and
    transferring communication signals using the second modulation parameter setting over the telemetry link between the implantable medical device and the external instrument, wherein transferring communication signals using a first initial modulation parameter setting over a telemetry link between the implantable medical device and the external instrument further comprises using a second initial modulation parameter setting, the method further comprising selecting a third modulation parameter setting as a replacement for the second initial modulation parameter setting in response to the analysis, and wherein transferring communication signals using the second modulation parameter setting over the telemetry link between the implantable medical device and the external instrument further comprises using the third modulation parameter setting in addition to the second modulation parameter setting.

14. The method of claim 13, wherein the first initial modulation parameter setting comprises a modulation type and wherein the second initial modulation parameter setting comprises a modulation symbol rate.

15. The method of claim 13, further comprising:
    analyzing a quality metric of the communication signals that have been transferred using the second modulation parameter setting;
    selecting a fourth modulation parameter setting as a replacement for the second modulation parameter setting in response to the analysis; and
    transferring communication signals using the fourth modulation parameter setting over the telemetry link between the implantable medical device and the external instrument.

16. A method of adapting communications between an implantable medical device and an external instrument, comprising:
    transferring communication signals using a first initial modulation parameter setting over a telemetry link between the implantable medical device and the external instrument;
    listening during a period of time when no communication signals are being transferred between the external device and the implantable medical device to obtain a signal strength reference;
    analyzing a quality metric of the communication signals that have been transferred, the analyzing comprising comparing the signal strength reference to a signal strength of the communication signals to obtain a signal-to-noise ratio for the telemetry link;
    selecting a second modulation parameter setting as a replacement for the first initial modulation parameter setting in response to the analysis;
    transferring communication signals using the second modulation parameter setting over the telemetry link between the implantable medical device and the external instrument,
    sending between the external instrument and the implantable device a communication signal using the first initial modulation parameter setting that requests to change from the first initial modulation parameter setting to the second modulation parameter setting; and
    in response to the communication signal that requests to change, sending a responsive communication signal using the first initial modulation parameter setting.

17. A method of adapting communications between an implantable medical device and an external instrument, comprising:
    transferring communication signals using a first initial modulation parameter setting over a telemetry link between the implantable medical device and the external instrument;
    listening during a period of time when no communication signals are being transferred between the external device and the implantable medical device to obtain a signal strength reference;
    analyzing a quality metric of the communication signals that have been transferred, the analyzing comprising comparing the signal strength reference to a signal strength of the communication signals to obtain a signal-to-noise ratio for the telemetry link;
    selecting a second modulation parameter setting as a replacement for the first initial modulation parameter setting in response to the analysis; and
    transferring communication signals using the second modulation parameter setting over the telemetry link between the implantable medical device and the external instrument, wherein selecting a second modulation parameter setting as a replacement for the first initial modulation parameter setting in response to the analysis comprises selecting the second modulation parameter setting for use by only the external instrument when transmitting and only the implantable medical device when receiving and wherein transferring communication signals using the second modulation parameter setting over the telemetry link between the implantable medical device and the external instrument comprises transmitting communication signals using the second modulation parameter setting over the telemetry link only by the external instrument and receiving communication signals using the second modulation parameter setting over the telemetry link only by the implantable medical device.

18. A method of adapting communications between an implantable medical device and an external instrument, comprising:
- transferring communication signals using a first initial modulation parameter setting over a telemetry link between the implantable medical device and the external instrument;
- listening during a period of time when no communication signals are being transferred between the external device and the implantable medical device to obtain a signal strength reference;
- analyzing a quality metric of the communication signals that have been transferred, the analyzing comprising comparing the signal strength reference to a signal strength of the communication signals to obtain a signal-to-noise ratio for the telemetry link;
- selecting a second modulation parameter setting as a replacement for the first initial modulation parameter setting in response to the analysis; and
- transferring communication signals using the second modulation parameter setting over the telemetry link between the implantable medical device and the external instrument, wherein selecting a second modulation parameter value as a replacement for the first initial modulation parameter setting in response to the analysis comprises selecting the second modulation parameter for use by only the implantable medical device when transmitting and only by the external instrument when receiving and wherein transferring communication signals using the second modulation parameter setting over the telemetry link between the implantable medical device and the external instrument comprises transmitting communication signals using the second modulation parameter setting over the telemetry link only by the implantable medical device and receiving communication signals using the second modulation parameter setting over the telemetry link only by the external instrument.

19. A method of adapting communications between an implantable medical device and an external instrument, comprising:
- transferring communication signals using a first initial modulation parameter setting over a telemetry link between the implantable medical device and the external instrument;
- listening during a period of time when no communication signals are being transferred between the external device and the implantable medical device to obtain a signal strength reference;
- analyzing a quality metric of the communication signals that have been transferred, the analyzing comprising comparing the signal strength reference to a signal strength of the communication signals to obtain a signal-to-noise ratio for the telemetry link;
- selecting a second modulation parameter setting as a replacement for the first initial modulation parameter setting in response to the analysis; and
- transferring communication signals using the second modulation parameter setting over the telemetry link between the implantable medical device and the external instrument, wherein transferring communication signals using the second modulation parameter setting over the telemetry link between the implantable medical device and the external instrument comprises transferring communication signals from the external instrument to the implantable medical device, the method further comprising:
- listening at the external instrument for a response by the implantable medical device; and
- when the external instrument does not receive a valid response by the implantable medical device, then selecting the first initial modulation parameter setting and at a subsequent time transferring communication signals from the external instrument to the implantable medical device using the first initial modulation parameter setting.

20. The method of claim 19, further comprising:
- listening at the implantable medical device for communication signals using the second modulation parameter setting from the external instrument;
- when the implantable medical device does not receive a valid communication signal that uses the second modulation parameter setting, then at a subsequent time listening at the implantable medical device for communication signals using the first initial modulation parameter setting.

21. A method of adapting communications between an implantable medical device and an external instrument, comprising:
- transferring communication signals using a first initial modulation parameter setting over a telemetry link between the implantable medical device and the external instrument;
- listening during a period of time when no communication signals are being transferred between the external device and the implantable medical device to obtain a signal strength reference;
- analyzing a quality metric of the communication signals that have been transferred, the analyzing comprising comparing the signal strength reference to a signal strength of the communication signals to obtain a signal-to-noise ratio for the telemetry link;
- selecting a second modulation parameter setting as a replacement for the first initial modulation parameter setting in response to the analysis;
- transferring communication signals using the second modulation parameter setting over the telemetry link between the implantable medical device and the external instrument,
- analyzing the quality metric of the communication signals that have been transferred using the second modulation parameter setting and a second initial modulation parameter setting;
- selecting a third modulation parameter setting as a replacement for the second initial modulation parameter setting in response to the analysis; and
- transferring communication signals using the second modulation parameter setting and the third modulation parameter setting over the telemetry link between the implantable medical device and the external instrument.

22. The method of claim 21, wherein the second modulation parameter setting comprises a modulation type and wherein the third modulation parameter setting comprises a modulation symbol rate.

23. A method of adapting communications between an implantable medical device and an external instrument, comprising:
- transferring communication signals using a first initial modulation parameter setting over a telemetry link between the implantable medical device and the external instrument;

listening during a period of time when no communication signals are being transferred between the external device and the implantable medical device to obtain a signal strength reference;

analyzing a quality metric of the communication signals that have been transferred, the analyzing comprising comparing the signal strength reference to a signal strength of the communication signals to obtain a signal-to-noise ratio for the telemetry link;

selecting a second modulation parameter setting as a replacement for the first initial modulation parameter setting in response to the analysis; and transferring communication signals using the second modulation parameter setting over the telemetry link between the implantable medical device and the external instrument, wherein transferring a communication signal using the first initial modulation parameter setting over the telemetry link comprises:

transferring a first communication signal from the external instrument to the implantable medical device over the telemetry link; and transferring a second communication signal from the implantable medical device to the external instrument in response to the first communication signal over the telemetry link; and wherein analyzing the quality metric occurs at the implantable medical device by analyzing the first communication signal.

24. A method of adapting communications between an implantable medical device and an external instrument, comprising:

transferring communication signals using a first initial modulation parameter setting over a telemetry link between the implantable medical device and the external instrument;

listening during a period of time when no communication signals are being transferred between the external device and the implantable medical device to obtain a signal strength reference;

analyzing a quality metric of the communication signals that have been transferred, the analyzing comprising comparing the signal strength reference to a signal strength of the communication signals to obtain a signal-to-noise ratio for the telemetry link;

selecting a second modulation parameter setting as a replacement for the first initial modulation parameter setting in response to the analysis; and transferring communication signals using the second modulation parameter setting over the telemetry link between the implantable medical device and the external instrument, wherein selecting a second modulation parameter setting as a replacement for the first initial modulation parameter setting in response to the analysis comprises choosing the second modulation parameter setting based on a type of application for the communication signals.

* * * * *